United States Patent [19]

Dolbier, Jr. et al.

[11] Patent Number: 5,210,341
[45] Date of Patent: May 11, 1993

[54] PROCESSES FOR THE PREPARATION OF OCTAFLUORO-[2,2]PARACYCLOPHANE

[75] Inventors: William R. Dolbier, Jr.; M. A. Asghar; He-Qi Pan, all of Gainsville, Fla.

[73] Assignee: Union Carbide Chemicals & Plastics Technology Corporation, Danbury, Conn.

[21] Appl. No.: 812,575

[22] Filed: Dec. 20, 1991

[51] Int. Cl.$^5$ ............................................. C07C 22/00
[52] U.S. Cl. ..................................... 570/144; 570/129
[58] Field of Search ............... 570/143, 144, 129, 148, 570/149, 128

[56] References Cited

U.S. PATENT DOCUMENTS

| | | | |
|---|---|---|---|
| 3,268,599 | 8/1966 | Chow | 260/649 |
| 3,274,267 | 9/1966 | Chow | 260/649 |
| 3,297,591 | 1/1967 | Chow | 260/2 |
| 4,849,559 | 7/1989 | Lee et al. | 570/199 |
| 5,110,903 | 5/1992 | Lee et al. | 570/190 |

OTHER PUBLICATIONS

Chow, Pilato and Wheelwright, The Synthesis of 1,1,2,2,9,9,10,10,Octafluoro-[2,2]paracyclophane, The Journal of Organic Chemistry, vol. 35, No. 1, 20–22, Jan. 1970.
Cooper, Reductive Coupling of Arkyl Halides by Vanadium (II), Journal of the American Chemical Society, 4158–4162, Jun. 27, 1973.
Olah and Prakash, Synthetic Methods and Reactions; XVIII, Preparation of Alkenes via Dehalogenation of vic-Dihaloalkanes, Coupling of Allyl and Benzyl Halides, . . . Communications, 607–609, Sep., 1976.
Ho and Olah, Synthetic Methods and Reactions; 34. Coupling of Benzylic and Allylic Halides and Debromination of vic-Dibromides with Vanadium (III) Chloride/Lithium Tetrahydroaluminate, . . . Communications, 170–171, Mar. 1977.
Eisch and Piotrowski, The Titanocene Methylene-Zinc Halide Complex: A Convenient Synthesis and its Methylenating Action on Unsaturated Carbon Centers, Tetrahydron Letters, vol. 24, No. 20, 2043–2046, 1983.
Pons and Santelli, Tetrahedron Report No. 237, Tetrahedron, vol. 44, No. 14; 4295–4312, 1988.

*Primary Examiner*—Marianne M. Cintins
*Assistant Examiner*—Rebecca Cook
*Attorney, Agent, or Firm*—W. K. Volles

[57] ABSTRACT

Processes are disclosed for the preparation of octafluoro-[2,2]paracyclophane which utilize a low temperature, e.g., less than about 200° C., and a reducing agent comprising titanium to promote the dimerization of dihalo-tetrafluoro-p-xylenes. One suitable reducing agent is prepared by combining $TiCl_4$ with $LiAlH_4$ in an organic solvent.

17 Claims, No Drawings

PROCESSES FOR THE PREPARATION OF OCTAFLUORO-[2,2]PARACYCLOPHANE

FIELD OF THE INVENTION

The present invention relates to processes for the preparation of octafluoro-[2,2]paracyclophane. More specifically, the present invention relates to low temperature processes for the preparation of octafluoro-[2,2]paracyclophane using a reduced form of titanium.

BACKGROUND OF THE INVENTION

Parylene is a generic term often used to describe a class of poly-p-xylenes which are derived from a dimer of the structure:

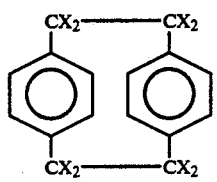

wherein X is typically hydrogen or a halogen.

Due to its ability to provide thin films and conform to substrates of varied geometric shapes, parylene is ideally suited for use as a conformal coating in a wide variety of fields, such as, for example, in the electronics, automotive, and medical industries. Parylene coatings are inert, transparent and have excellent barrier properties. When X in the above formula is hydrogen, parylene is particularly useful at temperatures of up to about 130° C.

Octafluoro-[2,2]paracyclophane ("AF4") is a fluorine substituted version of the above dimer and has the structure;

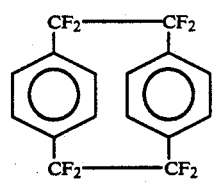

Parylene which is made from AF4 can also provide an inert, transparent conformal coating which has excellent barrier properties. In addition, parylene made from AF4 can be used at temperatures up to about 240° C.

Accordingly, parylene made from AF4 is particularly useful for coating products that will be exposed to high temperatures, e.g., electrical components in automotive applications. However, despite the commercial need, AF4 has not been extensively used as a dimer for the production of parylene because the typical preparation method for AF4 involves pyrolyzing a monomer at temperatures in the range of about 600 to 1000° C. These high temperatures have made the process uneconomical. The following patents describe the preparation of AF4 under pyrolysis conditions.

U.S. Pat. No. 3,268,599, issued to Chow, relates to a process for the preparation of cyclic alpha-perfluoro-di-p-xylylenes, specifically AF4, by the pyrolysis of a dihalide monomer. At column 1, line 51 to column 2, line 6, the patentee discloses;

Now in accordance with the present invention, cyclic α-perfluoro-di-p-xylylene having the structural formula

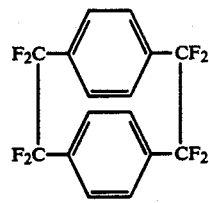

is produced by the process which comprises forming a reactive intermediary p-xylylene diradical having the basic structure

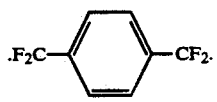

by the pyrolysis at temperatures between about 700° C.–1000° C. of compounds having the general formula

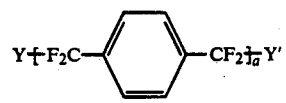

wherein Y is a halogen having a lower bond strength than fluorine such as bromine, chlorine, and iodine, and Y' is a member selected from the group consisting of hydrogen and a halogen having a lower bond strength than fluorine and n is an integer from 1 to 2 inclusive, and cooling and condensing the thus formed diradicals in intimate admixture with a fluid medium containing an inert organic solvent maintained at a temperature above about 50° C.

U.S. Pat. No. 3,274,267, issued to Chow, also relates to the preparation of AF4. However, the compounds disclosed in U.S. Pat. No. 3,274,267 have an aromatic nuclear substituent group on each of the benzene rings.

U.S. Pat. No. 3,297,591, issued to Chow, relates to a process for the preparation of parylene made from AF4 and contains a similar disclosure to U.S. Pat. No. 3,268,599 with regard to the preparation of AF4 by pyrolysis.

Chow, Pilato and Wheelwright in an article captioned *The Synthesis of 1,1,2,2,9,9,10,10,-Octafluoro [2,2]paracyclophane*, The Journal of Organic Chemistry, Volume 35, No. 1, 20–22, Jan., 1970, disclose a method for the preparation of AF4 which is similar to the method described in the above patents.

In order to allow for more widespread use of parylene made from AF4, it is desirable to produce AF4 by processes which can operate at low temperatures, i.e., non-pyrolysis conditions.

SUMMARY OF THE INVENTION

By the present invention processes for the preparation of AF4 are provided which utilize a low temperature in conjunction with a reduced form of titanium in order to promote dimerization of dihalide monomers. Thus, by virtue of the present invention it is no longer necessary to Pyrolize dihalide monomers in order to obtain AF4.

In one aspect of the present invention there is provided a process for the preparation of octafluoro-[2,2]paracyclophane, which comprises contacting a dihalo-tetrafluoro-p-xylene with an effective amount of a reducing agent comprising a reduced form of titanium and an organic solvent at conditions effective to promote the formation of a reaction product comprising octafluoro-[2,2]paracyclophane.

Preferably, the contacting is performed at a temperature less than about 200° C. and more preferably from about 20 to about 100° C. In addition, it is preferred that the dihalo-tetrafluoro-p-xylene is dibromo-tetrafluoro-p-xylene. It is further preferred that the reducing agent is prepared from $TiCl_4$ and $LiAlH_4$. Quite surprisingly, it has been found that the reduced form of titanium is uniquely effective in promoting the dimerization of dibromo-tetrafluoro-p-xylene to form AF4.

DETAILED DESCRIPTION OF THE INVENTION

The reducing agent of the present invention comprises a reduced form of titanium in an organic solvent. Typically, the reduced titanium will have a valence of from 0 to 3. Preferably, the reduced titanium is prepared by combining $TiCl_4$ and a lithium hydride in the organic solvent at conditions effective to reduce the valence of the titanium. Illustrative of the lithium hydride compounds are $LiAlH_4$ and $LiB(C_2H_5)_3H$, of which $LiAlH_4$ is preferred. Thus, in a preferred aspect of the invention, the reducing agent comprises lithium, aluminum and chloride ions in addition to the reduced titanium. When combining the $TiCl_4$ and $LiAlH_4$ in the organic solvent, it is preferred to provide equivalent molar quantities of $TiCl_4$ and $LiAlH_4$. Both $TiCl_4$ and $LiAlH_4$ are commercially available reagents and can be obtained, for example, from Aldrich Chemical Company, Atlanta, Georgia.

Preferably, the organic solvent used in preparing the reducing agent comprises one or more ethers. The particular ether, or mixture of ethers, used is not critical to the present invention, but is often selected based on the boiling point of the solvent. Typical ether solvents suitable for use in preparing the reducing agent include tetrahydrofuran ("THF"), dioxane and dimethoxyethane. Each of these solvents is commercially available. One particularly preferred organic solvent is THF, which is available, for example, from Aldrich Chemical Company, Atlanta, Georgia.

The conditions used for preparing the reducing agent are not critical to the present invention. However, the temperature should be maintained above the melting point and below the boiling point of the particular solvent used. Typically, the temperature range will be from about $-50°$ C. to about 100° C. In a preferred aspect of the invention wherein THF is the solvent, the temperature is preferably maintained at about 0° C, e.g., by an ice bath, while preparing the reducing agent. The pressure can be subatmospheric, atmospheric or superatmospheric pressure and typically, will range from about 0.1 to about 10 atmospheres. Pressures at or near atmospheric pressure are preferred. It is preferred to utilize an inert atmosphere, such as, for example, argon, nitrogen or helium when preparing the reducing agent.

The dihalo-tetrafluoro-p-xylene ("dihalide") can be prepared by halogenating $\alpha,\alpha,\alpha',\alpha'$-tetrafluorop-xylene. Halogenation of $\alpha,\alpha,\alpha',\alpha'$-tetrafluoro-p-xylene can be accomplished by introducing a halogen substituent having a lower bond strength than the fluorine already present in the alpha position. For example, when $\alpha,\alpha,\alpha',\alpha'$-tetrafluoro-p-xylene is employed, halogens such as chlorine, bromine, or iodine can be employed since they have lower bond strengths than fluorine.

Methods for preparing the dihalides are known in the art. See, for example, U.S. Pat. No. 3,268,599, issued to Chow. The resulting dihalides are often referred to as $\alpha,\alpha'$-dihalo-$\alpha,\alpha,\alpha',\alpha'$-tetrafluoro-p-xylenes. The bromine substituted dihalide, i.e., dibromo-tetrafluoro-p-xylene ("dibromide") is particularly preferred for use in the process of the present invention.

In the process of the present invention, a dihalide is contacted with the reducing agent at conditions effective to promote the formation of a reaction product comprising AF4 by dimerization of the dihalide. Preferably, the dihalide is added gradually to the reducing agent. The term "gradually", as used herein, means from about 2 to about 20 hours. More preferably, the dihalide is added to the reducing agent over a period of from about 4 to about 15 hours. As a result of the relatively slow addition rate, it is preferred to dilute the dihalide with a solvent, preferably an organic solvent. The particular solvent used to dilute the dihalide is not critical to the present invention, although it is preferred to use the same solvent or solvents as contained in the reducing agent in order to simplify the subsequent recovery of AF4.

Typically, an excess of the reducing agent will be provided relative to the dihalide. Preferably, the reducing agent will be present, throughout the reaction, in a molar ratio of at least 3 moles of titanium per mole of dihalide and more preferably, at least 4 moles of titanium per mole of dihalide. In addition, it is preferred that the amount of excess is effective to maximize the yield of AF4 without wasting the reducing agent. Typically, the molar ratio will be less than about 6 moles of titanium per mole of dihalide.

The effective conditions for promoting the formation of AF4 include a temperature which is lower than pyrolysis temperatures, i.e., lower than about 600° C. Preferably, the temperature is maintained at less than about 200° C. and more preferably, from about 20 to about 100° C. It is also preferred that the reaction be conducted under reflux conditions. Thus, the temperatures employed often correspond to the boiling point of the particular organic solvent used in the reducing agent, e.g., 76° C. for THF. The pressure used during the reaction is not critical to the Present invention and can be subatmospheric, atmospheric or superatmospheric. Typical pressures will be in the range of from about 0.1 atmospheres to about 10 atmospheres. It is preferred that contacting be performed in an inert atmosphere such as, for example, under nitrogen, helium or argon.

The recovery of the AF4 is relatively simple. It can, for example, be readily recovered by subliming it from a high boiling solvent such as mineral oil. One preferred method is to remove most of the organic solvent by distillation and then crystallize the AF4 from the remaining solvent by cooling and filtering off the crystallized AF4. Another preferred method is to isolate the AF4 by acid hydrolysis of the reaction product, followed by the extraction of the AF4 into methylene chloride, followed by evaporation of the solvent. Purification can than be readily accomplished by known methods, e.g., sublimation, column chromatography or recrystallization.

The yield of AF4, whether prepared by the process of the present invention or by pyrolysis, for example, is relatively modest. For example, yields of about 10 mole % based on ½ of the moles of dihalide, i.e., 2 moles of dihalide yield 1 mole of AF4, are not uncommon. Typically, in accordance with the present invention, the yield of AF4 is at least about 20 mole % and preferably from about 25 to about 35 mole %, based on ½ of the moles of dihalide.

The AF4 produced by the process of the present invention is particularly suitable for use as a dimer for the production of parylene. Parylene which is produced from AF4 can have a wide variety of applications, for example, in the electronics, automotive, and medical industries, but is particularly useful as a coating material which will be subjected to harsh environments. Typical harsh environments include exposure to the weather, salt, corrosive chemicals, etc. In addition, parylene made from AF4 can withstand temperatures of up to about 240° C., which makes it particularly suitable for high temperature applications, such as, for example, in the coating of electrical components, e.g., multi-chip modules, used near the engines in automobiles, trucks, boats, planes, and the like. Another suitable use for parylene made from AF4 is as a conformal coating on circuit boards used in harsh environments, such as, for example, in computers and process controllers in petroleum refineries and chemical plants.

The following examples are provided for illustrative purposes and are not intended to limit the scope of the claims which follow.

EXAMPLE 1

Preparation of dibromo-tetrafluoro-p-xylene: $\alpha,\alpha,\alpha'$-,$\alpha'$-tetrafluoro-p-xylene is prepared by the method of Hasek et al., Journal of the American Chemical Society, 82, 543 (1960), by the reaction of terephthalaldehyde with sulfur tetrafluoride at temperatures of about 150° C. 0.15 moles of $\alpha,\alpha,\alpha',\alpha'$-tetrafluoro-p-xylene as prepared above is admixed with 0.33 moles of N-bromosuccinimide and 320 parts of carbon tetrachloride. The mixture is irradiated with an ultraviolet lamp and maintained at the reflux temperature of the solvent. The precipitated succinimide is removed by filtration and the filtrate is distilled to give 0.12 moles of $\alpha,\alpha'$-dibromo-$\alpha,\alpha,\alpha',\alpha'$-tetrafluoro-p-xylene having a boiling point of 102-107° C. at 25 mm. Hg.

EXAMPLE 2

Preparation of dichloro-tetrafluoro-p-xylene:

A solution of 10.7 grams ("g") of $\alpha,\alpha,\alpha',\alpha'$-tetrafluoro-p-xylene in 100 milliliters ("ml") of carbon tetrachloride is irradiated with an ultraviolet lamp. The solution is maintained at the reflux temperature of the solvent by the heat of the ultraviolet lamp. Chlorine is passed into the solution until the color of the chlorine remains in solution, i.e., about 9g of chlorine. Irradiation is continued for an additional 30 minutes. The excess chlorine is purged from the solution by a stream of argon. Distillation of the reaction solution yields 11.6g of $\alpha,\alpha'$-dichloro-$\alpha,\alpha,\alpha',\alpha'$-tetrafluoro-p-xylene having a boiling point of 86-90° C. at 34 millimeters Hg.

EXAMPLE 3

Preparation of the Reducing Agent:

The reducing agent was prepared by adding 0.41g of LiAlH$_4$ in 100 ml of THF to 2.05g of TiCl$_4$ in 40 ml of THF while cooling the mixture in an ice bath and stirring continuously under an argon atmosphere for a period of about ½ hour. As the LiAlH$_4$ was added to the suspension of TiCl$_4$ in THF, the mixture went through a number of color changes, starting out as a yellow suspension, becoming green and ending up as a dark brown-black fine suspension.

EXAMPLE 4

Preparation of AF4 under reflux:

AF4 was prepared by gradually adding 1g of the dibromide, prepared in accordance with the procedure set forth in Example 1, in 450 ml of THF, to the reducing agent prepared in Example 3. The gradual addition of the dibromide to the reducing agent was effected over a period 6 hours, under reflux conditions (bath temperature ~76° C). The reaction product was allowed to reflux for 1/2 hour after the addition was completed.

EXAMPLE 5

Analysis and yield determinations:

Analysis and yield determinations were carried out by taking ⅓ of the reaction product of Example 4 and evaporating the THF to dryness using a rotary evaporator at room temperature. A nuclear magnetic resonance ("nmr") internal standard (trifluoromethylbenzene) was then added to this solid residue which was then extracted with 2 ml of CDCl$_3$. A $^{19}$F nmr analysis of this solution provided the yield of the reaction. The peak due to AF4 comprised 63% of the total fluorine signals in the $^{19}$F nmr spectrum of the reaction product. The $^{19}$F nmr spectrum of AF4 had a singlet at 118.75 ppm in CDCl$_3$ and in DMSO-d$_6$ at 116.53 ppm. The $^1$H nmr spectrum had a singlet at 7.16 ppm in CDCl$_3$ and in DMSO-d$_4$ at 7.28 PPm. The identity of the product was also certified by gas chromatography and mass spectrometry of the reaction product.

Isolation of the AF$_4$ was accomplished by evaporating 50% of the product mixture followed by adding 300-350 ml of dilute aqueous HCl. This mixture was extracted using methylene chloride and then washed with aqueous bicarbonate and dried. After evaporation, a dark residue remained. This residue was dissolved in a minimum amount of methylene chloride, and then passed through a short silica gel column, about 4 cm, to provide, after recrystallization from hexane, a light yellow solid which appeared to be 95-97 mole % pure by $^{19}$F nmr. The yield of AF4 was 32 mole % based on one-half of the moles of dibromide added to the reducing agent, i.e., two moles of dibromide are required to form one mole of AF4.

EXAMPLE 6

Preparation of AF4 at room temperature:

AF4 was prepared by gradually adding, over a period of 12 hours, 0.5g of dibromide, prepared in accordance with the procedure set forth in Example 1, in 470 ml of THF, to 3.6 equivalents of the reducing agent of Example 3 in 520 ml of THF. The crude product was isolated and had a purity of 95-97 mole % AF4. The yield of AF4, as determined by the method of Example 5, was 29 mole %.

EXAMPLE 7

Preparation of AF4 at 0° C:

AF4 was prepared in the same manner as that described in Example 6 except that the reaction temperature was maintained at about 0 to 5° C. The crude product was isolated and had a purity of 13 mole % AF4. The yield of AF4, as determined by the method of Example 5, was 6 mole %.

EXAMPLE 8

Substitution of THF with Dimethoxyethane:

AF4 was prepared according to the same procedure as described in Example 4 except the THF was replaced with dimethoxyethane and the reaction temperature was maintained at 60° C. The crude product was isolated and had a purity of 60 mole % AF4. The yield of AF4, as determined by the method of Example 5, was 28 mole %.

EXAMPLE 9

Preparation of AF4 with a Vanadium Reducing Agent:

A vanadium reducing agent was prepared by adding 2.7 ml of a 1 molar solution of $LiAlH_4$ in THF to 1.27g of $VCl_3$ in 100 ml of the THF in the same manner as described in Example 3. To this mixture was added 0.5g of the dibromide, prepared in accordance with the procedure set forth in Example 1, in 100 ml of THF. The gradual addition of the dibromide to the reducing agent was effected over a period of 10 hours with reflux. The reaction product was isolated and analyzed in accordance with the method described in Example 5. No AF4 was produced. Instead, it was found that the dibromide had undergone reduction to $\alpha,\alpha,\alpha',\alpha'$-tetrafluoro-p-xylene.

EXAMPLE 10

Use of Rieke Titanium in the Reducing Agent:

A suspension of a reducing agent was Prepared by adding 0.72g of metallic potassium to 0.85g of $TiCl_4$ in 100 ml of THF at 0° C. Then the mixture was refluxed overnight until a brown-black suspension was obtained. To this mixture was added 0.5g of the dibromide, prepared in accordance with the procedure set forth in Example 1, in 150 ml of THF gradually over a period of 18 hours at room temperature. The mixture was then stirred at room temperature for an additional 12 hours. After refluxing at 76° C. for another 12 hours, no AF4 was produced.

EXAMPLE 11

Use of lithium triethyl borohydride in the Reducing Agent:

A suspension of the reducing agent was prepared by adding 20.9 ml of a 1 molar solution of $LiB(C_2H_5)_3H$ in THF to 0.99g of $TiCl_4$ in 100 ml of THF at 0° C. under an argon atmosphere. To this mixture was added 0.5g of the dibromide, prepared in accordance with the procedure set out in Example 1, in 150 ml of THF gradually over a period of 12 hours at room temperature. The mixture was then stirred for an additional 20 hours at room temperature. The reaction product was isolated and analyzed in the same manner as described in Example 5. The crude Product was isolated and had a purity of 13 mole % AF4. The yield of AF4 was 3.4 mole %.

All of the dibromide was consumed. Other products included $\alpha,\alpha,\alpha',\alpha'$-tetrafluoro-p-xylene and possibly higher oligomers thereof.

EXAMPLE 12

Ue of dichloro-tetrafluoro-p-xylene to produce AF4:
Preparation of AF4 at 0° C:

AF4 is prepared by gradually adding dichlorotetrafluoro-p-xylene ("dichloride"), prepared in accordance with the procedure set forth in Example 2, in THF to the reducing agent prepared in Example 3. The addition of the dichloride to the reducing agent is effected under reflux conditions as described in Example 4.

We claim:

1. A process for the preparation of octafluoro-[2,2]paracyclophane, which comprises contacting a dihalo-tetrafluoro-p-xylene with a reducing agent comprising a reduced form of titanium, chloride ions, lithium ions and aluminum ions at a temperature of less than about 200° C. and effective conditions to promote the formation of a reaction product comprising octafluoroparacyclophane, wherein the yield of octafluoroparacyclophane is at least 20 mole % based on one-half of the moles of dihalo-tetrafluoro-p-xylene contacted with the reducing agent.

2. The process of claim 1 wherein the reducing agent is present in an amount of at least 3.0 moles of titanium per mole of the dihalotetrafluoro-p-xylene.

3. The process of claim 1 wherein the effective conditions include a temperature of from about 20 to about 100° C.

4. The process of claim 1 wherein the effective conditions include contacting the dihalo-tetrafluoro-p-xylene with the reducing agent under reflux conditions.

5. The process of claim 1 wherein the effective conditions include an inert atmosphere.

6. The process of claim 1 wherein the dihalo-tetrafluoro-p-xylene is added gradually to the reducing agent.

7. The process of claim 1 wherein the titanium has a valence of from 0 to 3.

8. The process of claim 1 wherein the reducing agent is prepared by combining $TiCl_4$ and $LiAlH_4$ in an organic solvent.

9. The process of claim 1 which further comprises recovering at least a portion of the octafluoro-paracyclophane from the reaction product.

10. The process of claim 1 wherein the yield of octafluoro-paracyclophane is at least from about 25 to about 35 weight % based on one-half of the moles of dihalo-tetrafluoro-p-xylene contacted with the reducing agent.

11. The process of claim 1 wherein the dihalo-tetrafluoro-p-xylene is dibromotetrafluoro-p-xylene.

12. The process of claim 1 wherein the reducing agent is prepared by combining a first mixture comprising $TiCl_4$ and tetrahydrofuran with a second mixture comprising $LiAlH_4$ and tetrahydrofuran at conditions effective to provide titanium having a valence state of from 0 to 3.

13. The process of claim 12 wherein the effective conditions to provide titanium having a valence state of from 0 to 3 include a temperature of about 0° C.

14. The process of claim 12 wherein the effective conditions to provide titanium having a valence state of from 0 to 3 include an inert atmosphere.

15. The process of claim 8 wherein the organic solvent is selected from tetrahydrofuran, dioxane, dimethoxyethane and mixtures thereof.

16. A process for the preparation of octafluoroparacyclophane, which comprises:
(a) gradually adding a mixture of dibromotetrafluoro-p-xylene and tetrahydrofuran to a reducing agent comprising titanium having a valence of 0 to 3, tetrahydrofuran, lithium ions, aluminum ions and chloride ions, under an inert atmosphere and at a temperature less than about 200° C. to form a reaction product comprising octafluoro-paracyclophane, wherein the yield of octafluoro-paracyclophane is at least 20 mole % based on one-half of the moles of dihalotetrafluoro-p-xylene contacted with the reducing agent; and (b) recovering at least a portion of the octafluoro-paracyclophane from the reaction product.

17. The process of claim 16 wherein the temperature is from about 20 to about 100° C.

* * * * *